United States Patent [19]

Wood et al.

[11] Patent Number: 4,710,467
[45] Date of Patent: * Dec. 1, 1987

[54] PROCESS FOR PREPARING PHENYLALANINE

[75] Inventors: Louis L. Wood, Rockville; Gary J. Carlton, Elkridge, all of Md.

[73] Assignee: Purification Engineering, Inc., Columbia, Md.

[*] Notice: The portion of the term of this patent subsequent to Mar. 13, 2001 has been disclaimed.

[21] Appl. No.: 640,778

[22] Filed: Aug. 14, 1984

Related U.S. Application Data

[63] Continuation-in-part of Ser. No. 518,756, Jul. 29, 1983, Pat. No. 4,600,692, which is a continuation-in-part of Ser. No. 465,551, Feb. 10, 1983, and Ser. No. 358,784, Mar. 16, 1982, Pat. No. 4,436,813.

[51] Int. Cl.$^4$ .................... C12P 13/22; C12N 11/08; C12N 11/04
[52] U.S. Cl. .................................. 435/108; 435/180; 435/182
[58] Field of Search ............... 435/108, 116, 174, 177, 435/178, 180, 182

[56] References Cited

U.S. PATENT DOCUMENTS

| | | | |
|---|---|---|---|
| 3,183,170 | 5/1965 | Kitai et al. | 435/108 |
| 4,436,813 | 3/1984 | Wood et al. | 435/109 |
| 4,450,233 | 5/1984 | Mimurz et al. | 435/178 |
| 4,518,692 | 5/1985 | Rozzell | 435/108 X |

FOREIGN PATENT DOCUMENTS

| | | |
|---|---|---|
| 89165 | 9/1983 | European Pat. Off. |
| 1556584 | 11/1979 | United Kingdom |
| 2048266 | 12/1980 | United Kingdom |
| 2084155 | 4/1982 | United Kingdom |

OTHER PUBLICATIONS

Yamadz et al., Applied and Environmental Microbiology, vol. 42, No. 5, 1981, pp. 773-778.
Jack, et al., Advances in Biochem. Eng., vol. 5, 1977, pp. 126-135.
Porath, et al., Methods In Enzmology, vol. XLIV, 1976, pp. 19-45.
Chemical Abstracts, vol. 57, Jul. 23, 1962, col. 2680a-b.
Chemical Abstracts, vol. 95, Dec. 28, 1981, p. 4, ref. 220379g.
Biotechnology and Bioengineering, vol. XXV, Apr. 1983, pp. 999-1011, John Wiley & Sons, Inc. (US)
Won-Gi Bang et al, "Production of L-tryptophan by Escherichia Coli Cells".
Chemical Abstracts, vol. 58, Jun. 10, 1963, col. 13094f.
Chemical Abstracts, vol. 74, Jan. 18, 1971, p. 37, ref. 9893d.
Chemical Abstracts, vol. 79, Nov. 26, 1973, p. 10, ref. 126931d.
Journal of Membrane Science, vol. 11, No. 3, Oct. 1982, pp. 365-370, E. Drioli et al.: "High-Temperature Immobilized-Cell Ultrafiltration Reactors".
Chemical Abstracts, vol. 66, Apr. 24, 1967, p. 7201, ref. 76541k.
Biochemistry, vol. 13, No. 19, 1974, pp. 3859-3863, "Irreversible Inhibition of Aspartate Aminotransferase by 2-Amino-3-Butenoic Acid", by Robert R. Rando.
Applied Biochemistry and Biotechnology 8, (1983) pp. 135-144, "Comparison of the Coupling Recoveries of Immobilized Aspartate Aminotransferase", by K. Kurkijarvi et al.
The Journal of Biochemistry, vol. 43, No. 6, 1956, pp. 851-855, "Enzymatic Preparation of Optically Active Essential Amino Acids", Setsuji Sakurai.
Phenylalanine and Tyrosine, Chapter 16, by Kunio Oishi, from The Microbial Production of Amino Acids, ed. by Yamada, et al., 1972, pp. 435-452.
Eur. J. Biochem. 87, Janet T. Powell et al, pp. 391-400.
Shiio et al., Agric. Biol. Chem. 46(12), pp. 2967-2977, 1982.
Gelfand et al., Journal of Bacteriology, Apr. 1977, pp. 429-440.
Serge Chesne et al., Biochimie, 1975, 57, pp. 1029-1034.
Bernard Bulos et al., The Journal of Biological Chemistry, vol. 240, No. 8, Aug. 1965, pp. 3283-3294.
Henson et al., Biochemistry 3, (1964), pp. 338-345.
Canellakis et al., J. Biol. Chem. 222, pp. 53-62 (1956).
S. Chesne et al., Biochmie, 1978, 60, pp. 403-407.

Primary Examiner—David M. Naff
Attorney, Agent, or Firm—Cushman, Darby & Cushman

[57] ABSTRACT

Phenylalanine is prepared by contacting phenylpyruvic acid or phenylpyruvate with an enzyme having transaminase activity in the presence of an amine donor. The enzyme may be free or immobilized or in whole cells which may be free or immobilized. The enzyme is preferably contained by E. coli ATCC 11303. Yield of phenylalanine can be improved by removing oxaloacetate, produced during reaction of the enzyme, to drive the reaction to completion. Phenylalanine may also be produced from cinnamic acid using immobilized cells having phenylalanine ammonia lyase activity.

1 Claim, No Drawings

PROCESS FOR PREPARING PHENYLALANINE

This application is a continuation-in-part of Ser. No. 518,756 filed July 29, 1983 now U.S. Pat. No. 4,600,692, which is in turn a continuation-in-part of Ser. No. 465,551, filed Feb. 10, 1983, and a continuation-in-part of Ser. No. 358,784, filed Mar. 16, 1982 now U.S. Pat. No. 4,436,813. The disclosures of these earlier applications are incorporated herein by reference.

The present invention is primarily concerned with the production of phenylalanine from a precursor thereof, notably phenylpyruvate or phenylpyruvic acid, via transaminase. One embodiment of the invention utilizes immobilized whole cells having transaminase activity to produce phenylalanine from phenylpyruvate. However, according to a further embodiment of the invention, the desired enzyme activity may be obtained by using whole, unruptured or permeabilized cells, as such or as purified fractions thereof, either in the free or immobilized state to obtain phenylalanine.

The invention also contemplates the possibility of preparing phenylalanine from cinnamic acid using immobilized whole cells having phenylalanine ammonia lyase activity.

The production of phenylalanine from phenylpyruvate has been attempted by numerous investigators. There are two possible routes to accomplish this transformation. One is by transamination with an appropriate amine donor while the other is direct reductive amination using a biological energy source such as NAD or NADP.

Sakurai (J. Biochemistry 43, 851, 1956) attempted the preparation of optically active amino acids via transamination. Sakurai used crude pig heart transaminase (freshly obtained) and found that after 20 hours the yield of phenylalanine reached a maximum of 58% (after subtracting the control value) when aspartic acid was used with a small amount of glutamic acid. When aspartic acid alone was used, the yield was only 44% (after subtracting the control value). Sakurai concluded that both amino acids should be present for maximal yields. He explained this result as a coupled system in which glutamic acid was the amine donor for phenylalanine and the aspartic acid served to regenerate the glutamic acid.

Oishi ("The Microbial Production of Amino Acids", John Wiley & Sons, K. Yamada et al Eds. 1972, Chap. 16) reviewed the production of phenylalanine from precursor keto acids. He noted a maximum yield of 63.5% phenylalanine was obtained by Asai in screening a large number of microbes which had been dried. This yield was obtained from a strain of *Alcaligenes faecalis*. The two strains of *E. coli* surveyed showed a 38.5% and a 53% yield under the reaction conditions used. Asai obtained yields of phenylalanine as high as 70.6% when the amine donor was a combination of L-aspartate, L-glutamate and L-leucine and the reaction had proceeded to its equilibrium. Yields with aspartate in twofold excess were only 54.5%.

It will be appreciated that the yields noted above with respect to the indicated prior procedures are not suitable for an economic industrial process. Yields in excess of 90% are generally considered essential for a commercially viable process.

Oishi also reported that, by using a coupled enzyme system, Kitai was able to reach 76.8% yield. The coupled system was a yeast alcohol dehydrogenase with beef liver glutamate dehydrogenase and the *Serratia marscescens* glutamatephenylalanine amino transferase. The reaction was driven by the removal of acetaldehyde by semicarbazide. Additionally, Kitai was able to drive the reaction to the expected 100% yield of L-phenylalanine by use of a coupled system for reductive amination in which *E. coli* were used to provide NADP. Glutamate, which served as the amine donor, was the limiting reagent.

Wandrey et al (U.S. Pat. No. 4,304,858) describe a coupled system (with formate dehydrogenase) for the production of phenylalanine from phenylpyruvate while providing exogenous NAD or NADH. The system is also applicable when using alpha-hydroxycarboxylic acid for the precursor as illustrated in U.S. Pat. No. 4,326,031. In both of these systems, however, it is necessary to use the reagent NAD or NADH and to use a coupled system in order to regenerate this expensive and labile material.

The available literature reviewed above indicates that only when using coupled systems are high yields of phenylalanine obtained from phenylpyruvate. When uncoupled systems are used, yields no higher than 71% have been obtained using three different amine donors.

This is expected on the basis of the available literature on transaminase from different sources. For instance, Bulos and Handler (The Journal of Biological Chemistry, Vol. 240, No. 8, pages 3283–3294, August 1965) found that beef heart glutamic-alanine transaminase which catalyzes the reaction:

had an equilibrium constant of 2.2. In a system of 0.1 m alanine and 0.15 m α-ketoglutarate, the formation of glutamate would be limited to 70%. Henson and Cleland (Biochemistry 3, pages 338–345, 1964) determined that pig heart glutamic oxaloacetic transaminase which catalyzes the reaction:

had an equilibrium constant of 0.16–0.17. Thus, a system of 0.1 m α-ketoglutarate and 0.15 m L-aspartate would reach an equilibrium at 32% conversion of the α-ketoglutarate to glutamate.

Canellakis and Cohen (J. Biol. Chem. 222, 53–62, 1956) examined dog liver tyrosine-α-ketoglutaric acid transaminase which catalyses the reaction:

p-hydroxyphenylpyruvic acid +

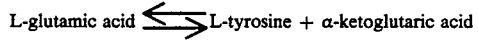

and found that equilibrium conditions were not attained after 3 hours and that the equilibrium is in favor of the formation of glutamic acid and p-hydroxyphenylpyruvic acid.

An important object of the invention is to provide a process for the production of phenylalanine in high yields with phenylpyruvic acid or phenylpyruvate via transaminase. A more specific object is to prepare phenylalanine by such a process which involves a single step, with a single amine donor and requiring neither a coupled system nor the addition of expensive cofactor reagents such as NADP or NAD. Other objects will also be hereinafter apparent.

According to the invention, phenylalanine is produced from phenylpyruvic acid or phenylpyruvate by transaminase using immobilized whole cells. In another embodiment of the invention, cells are used which are free in solution or which have been ruptured or permeabilized so as to release their transaminase activity. These ruptured or permeabilized cells may be in the free or immobilized state.

In our above-mentioned earlier applications, we have described the preparation and use of compositions comprising whole cells having enzymatic activity wherein the cells are immobilized by means of an insoluble, crosslinked polymer obtained by curing a polyazetidine prepolymer, carboxymethyl cellulose, polyurethane hydrogel prepolymer or polymethylene isocyanate. Preferably the immobilizing polymer is a polyazetidine polymer although the other disclosed polymers may be used. Advantageously the immobilized cells are coated onto beads or other particulate material.

For example, Ser. No. 465,551 describes the immobilization of cells using polyazetidine prepolymers which may be cross-linked in aqueous solution by reaction with $\leq NH$, $-SH$, $-OH$, $-COOH$; or other polyazetidines which may be crosslinked by $H_2O$ removal, heat, or by changing to a more basic pH. The following is an idealized structure of a representative polyazetidine such as Polycup ® 172 (Hercules, Inc.) which is useful for present purposes:

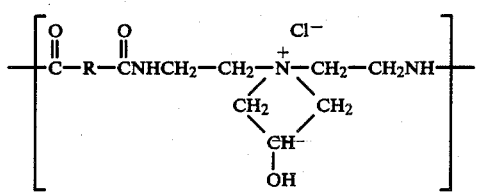

where R is typically $-(CH_2)_4-$.

The present invention contemplates the use of immobilized cell compositions as described in said earlier applications, as well as other forms of free or immobilized cells, provided the cells have transaminase activity. According to the invention, phenylalanine is produced by contacting a phenylalanine precursor, specifically phenylpyruvate or phenylpyruvic acid, with the cell composition having transaminase activity in the presence of an amine donor, so that the precursor is converted to phenylalanine. The literature indicates that small amounts of pyridoxal-5-phosphate (P5P) are required by the transaminase as a co-factor. This material (P5P) is also used in the present process in conventional co-factor amounts.

The precursor may be used in the form of the free acid or as a salt thereof, e.g. the ammonium or alkali metal salt.

A wide variety of amine donors may be used provided these are active with the transaminase. Preferably the donor is L-glutamic acid, L-aspartic acid or mixture thereof. However, other amine donors such as L-leucine or L-isoleucine may also give highly useful results. Preferably the donor is used in excess and it appears that higher yields are obtained as the excess is increased up to, for example, 30-50% excess or even more.

Any microorganism demonstrating transaminase activity may be used for present purposes. A wide variety of these are known (see Table 16-3, page 441, of Oishi publication mentioned above). These include the following:

Alcaligenes faecalis
Pseudomonas cruciviae
Pseudomonas aeruginosa MT
Aerobacter aerogenes
Escherichia coli
Achromobacter cycloclastes
Sarcina lutea
Kluyvera citrophila
Pseudomonas fluorescens
Micrococcus lysodeikticus.

The reaction conditions used for carrying out the transaminase reaction according to the invention can be widely varied, as will be understood by those in the art. For example, an aqueous solution of the precursor can be passed through a column containing the immobilized cells containing transaminase activity and the amine donor. Optimum ratios of precursor to donor and to cells, and other operating conditions, can be readily determined for any specific situation without undue experimentation. Typically, however, the ratio of the amine donor to the precursor will be at least 1:1 and preferably 1.1:1 or higher, e.g., 3:1. A preferred ratio is 1.5-2 parts donor per part precursor, parts being on an equivalent weight basis.

Acid or alkaline pHs may be used although there will generally be a readily determined optimum pH for any particular set of conditions. Usually it is desirable to use a pH above 4, and generally one in the range of 5-10, although pHs outside these ranges may also be used. Temperatures of 10° to 55° C. normally will be used although any temperature below transaminase deactivation can be used.

The invention is illustrated by the following examples:

EXAMPLE 1

*Saccharomyces cerevisiae, E. coli, Alcaligenes faecalis* and *Pseudomonas dacunhae* cells were immobilized in separate batches with polyazetidine as described in Ser. No. 465,551 (see, for instance, Example 8 thereof) by mixing equal parts of cell paste and aqueous polyazetidine solution (Hercules Polycup 172), stirring to homogenity at 25° C. by hand mixing with a wooden stick. The mixture was dispersed on Amberlite ion exchange beads which had been air-dried. The thin film of paste/prepolymer mixture on the beads was allowed to air dry at 25° C. One ml of each group of beads containing 0.2 grams of microbial cells per ml of beads was then placed into a 50 ml Erlenmeyer flask containing 25 ml of a 0.1M aqueous solution of sodium pyruvate and either L-glutamic acid, L-aspartic acid or mixture thereof as amine donor and 0.1 mM of P5P. These were then compared under otherwise similar conditions. The results in terms of phenylalanine (PHE) produced were determined by HPLC analysis of the supernatant after 17 hours of shaking and are presented below in Table I.

TABLE I

Transamination of Phenylpyruvic Acid (PPA) to Yield Phenylalanine (PHE)

| Microbe | Concentration PHE Formed Amine Donor: | | |
|---|---|---|---|
| | ASP & GLU | GLU | ASP |
| Saccharomyces cerevisiae | — | .012 M | <.002 M |
| E. coli | .024 M | .027 M | .013 M |
| A. faecalis | .01 M | .014 M | <.002 M |
| P. dacunhae | .024 M | .028 M | <.002 M |

(The references to "ASP" and "GLU" above represent L-aspartic acid and L-glutamic acid, respectively.)

The foregoing example demonstrates that whole cells immobilized as described and having transaminase activity may be effectively used to produce phenylalanine from phenylpyruvate precursor when an appropriate amine donor is employed.

In the control using P. dacunhae and A. faecalis in the fresh, wet free state (unruptured and unpermeabilized), negligible transaminase activity was noted. However, on rupturing the cells or by permeabilizing them, activity was substantially increased. This is surprising because the literature indicates that dried cells, which would normally be considered lysed or permeabilized, do not give commercially acceptable conversions.

Accordingly, the use of ruptured or permeabilized cells, whether immobilized or in the free state, to prepare phenylalanine constitutes a further aspect of the invention. Various techniques may be used to rupture or permeabilize the cells for use according to the invention. For example, the cells may be ruptured by sonication or grinding as known in the art. Alternatively the cells may be permeabilized by chemical treatment, e.g. by treatment with a permeabilizing surfactant such as Triton X100. These treatments apparently allow the phenylpyruvate or phenylpyruvic acid to more readily contact the enzyme and thus improve activity whether or not the microorganism is immobilized.

The use of ruptured cells, and the effect of pH and amine donor level in the results, are described in the following example:

EXAMPLE 2

2 grams of free E. coli cells were sonicated for 10 minutes in order to rupture the cells after which they were incubated for 23 hours with 25 ml aqueous solution containing different amounts of ASP (0.10M, 0.15M and 0.2M), 0.1 mM P5P and 0.1M PPA at 37° C. on a Dubnoff H2O shaker. H3PO4 was used for pH adjustment.

The results obtained are shown below in Table II.

TABLE II

| | ASP Level: | | |
|---|---|---|---|
| | .10 M | .15 M | .2 M |
| pH | % Conversion (PPA to PHE) | | |
| 7 | — | 87 | — |
| 8.4 | 77.6 | 90 | 96.7 |

As shown, free cells, when ruptured, give the best and most useful conversions at higher ASP concentrations, the data given in Table II indicating that for a commercially acceptable yield level, the amount of ASP should exceed the amount of substrate on a molar equivalence basis.

The various aspects of the invention are further illustrated by the following additional examples:

EXAMPLE 3

Table III shows the effect of pH on transaminase activity using E. coli whole cells immobilized in bead form as in Example 1. Three experiments were conducted using 2 ml of beads incubated in 15 ml of 0.1M PPA, 0.1 mM P5P and 0.15M ASP at 37° C. for 24 hours. The pH was adjusted with 1N NaOH or 1N HCl.

TABLE III

| Experiment 1 Immobilized Cells | | Experiment 2 Immobilized Cells | | Experiment 3 Free Cells | |
|---|---|---|---|---|---|
| pH | 24 hours % Conv. | pH | 4 hours Activity (units)* | pH | 4 hours Activity (units) |
| 5.0 | 95.9 | 3 | 32 | 3 | 78 |
| 5.5 | 96.5 | 4 | 99 | 4 | 94 |
| 6.0 | 95.0 | 5 | 219 | 5 | 123 |
| 6.5 | 95.9 | 6 | 212 | 6 | 601 |
| 7.0 | 95.1 | 7 | 217 | 7 | 598 |
| 8.0 | 94.7 | 8 | 207 | 8 | 571 |
| | | 9 | 209 | 8.4 | 586 |
| | | 10 | 156 | 9 | 637 |
| | | | | 10 | 115 |

*A unit is 1 micromol per hour per gram of wet cells.

The data in Table III shows that high yields of PHE similar to those obtainable with ruptured free cells can be obtained using immobilized E. coli.

EXAMPLE 4

Table IV below provides the results in terms of yield of PHE obtained using immobilized E. coli in a continuous column operation (300 ml, 3.5×70 cm) with 0.1M PPA, 0.15M ASP and 0.1 mM P5P.

TABLE IV

| Day | Experiment 1 | Experiment 2 |
|---|---|---|
| 1 | 95.1 | 100 |
| 8 | 91.2 | |
| 9 | 87.9* | |
| 10 | 92.1 | |
| 11 | 92.1 | 92 |
| 12 | 94.2 | |
| 13 | 95.1 | |
| 14 | 96.1 | |
| 15 | 94.8 | |
| 16 | 96.8 | |
| 17 | 95.8 | 85* |
| 18 | 95.3 | |
| 35 | | 91 |
| 42 | | 93 |
| 43 | | 97 |
| 45 | | 100 |

*It should be noted that occasional fluctuations in flow rates may show a reduced activity or yield on such occasions. However, the important factor is the maximum yield which is shown as this is indicative of the full potential of the process exemplified.

EXAMPLE 5

While polyazetidine polymer is preferred for immobilizing the microorganisms for use herein, the invention contemplates the possibility of using any other suitable immobilizing substrate. As representative of such alternatives, there may be mentioned such materials as polyacrylamide, Kappa-carrageenan, hollow fiber devices, Hypol or XAD coated beads. These materials have been shown to give excellent yields although the activity of the immobilized cells may vary from one immobilizing substrate to another. The results obtained in terms of yields and activities, using different systems involving immobilized E. coli, are shown below in Table V. The process used involved continuous flow onto a column of immobilized cells as described of an aqueous solution of 0.1M PPA, 0.15M ASP and 0.1 mM P5P at a pH 8.3–8.5 (adjusted with NH4OH) at 37° C. Flow varied according to column activity and space occupied. Equilibrium was reached at optimal flow prior to taking readings.

TABLE V

| Cell Immobilization Method | Observed | Max. Yield Activity (Units)* |
|---|---|---|
| E. coli coated on XAD beads with Polycup | 91 | 34 |
| E. coli coated on IRA938 beads with Polycup | 98 | 63 |
| E. coli with HYPOL foam | 95 | 53 |
| E. coli with Kappa-carrageenan gum | 100 | 29 |
| E. coli in a hollow fiber device | 91 | 82 |

*1 unit of activity is defined as 1 μmole/hr/g cells (wet wt.) at maximum conversion.

Of the materials referred to in Table V, XAD is a macroreticular styrene-divinylbenzene resin; IRA 938 is an ion exchange bead resin comprising styrene-divinylbenzene containing tertiary amine substituents; and Hypol is a polyurethane foam. The Kappa-carrageenan gum was cut into particles before use. The hollow fiber device was a commercially available item.

As an alternative to the procedures described above, phenylalanine may be made from cinnamic acid by using immobilized whole cells which are high in phenylalanine ammonia-lyase activity. This aspect of the invention represents an improvement in the process described by Yamada et al, Applied and Environmental Microbiology November 1981, pages 773–778, incorporated herein by reference.

EXAMPLE 6

Yamada et al describe the preparation of L-phenylalanine from trans-cinnamic acid by an enzymatic method using *Rhodotorula glutinis* containing L-phenylalanine ammonia-lyase activity. According to the present invention, *Rhodotorula glutinis* ATCC 10788 was grown as described by Yamada et al and the harvested cells were immobilized with polyazetidine prepolymer. 14.9 grams of cells were mixed with 14.9 grams of polyazetidine prepolymer and coated onto 13.8 grams of IRA 938 ion exchange resin and assayed for phenylalanine ammonia lyase activity. Cinnamic acid was added to the beads by mixing 1 ml of beads produced as above with 5 ml of assay mixture which contained 740 mg transcinnamic acid, 45 ml 28% ammonium hydroxide, pH 10 diluted to 80 ml. After 24 hours the supernatant was spotted on a cellulose TLC plate and developed in a mixture of butanol, acetic acid, water (4:1:1) and the plates were sprayed with 0.2% ninhydrin and ethanol. Standards of phenylalanine were used for comparison and an estimation based on intensity and size of the spot indicated that 0.5 mg/ml of phenylalanine had been produced.

According to still another feature of the invention, it has been found that the yield of phenylalanine (PHE) from phenylpyruvic acid (PPA) as such or as a salt thereof, e.g. sodium phenylpyruvate, can be greatly increased by contacting the starting material with an aromatic transaminase, preferably an aspartate transaminase, and subsequently driving the reaction by continuously removing one of the reactants.

Review of the literature on aromatic transamination shows that three major transaminating enzymes exist in *E. coli*. These are transaminase A which is actually two enzymes one of which is aspartate transaminase and the other of which is a tyrosine repressible aromatic transaminase, and transaminase B. Both of the transaminase A enzymes catalyze the formation of tryptophan, phenylalanine and tyrosine. Transaminase B catalyzes the formation of isoleucine, valine, norleucine and norvaline. [Powell & Morrison, Eur. J. Biochem. 87, 391–400 (1978)]

The aspartate transaminase, i.e. one of the two enzymes found in transaminase A, has been mapped on the *E. coli* chromosome at 20 min. and designated as an aspC mutation. The tyrosine repressible amino transferase is at 80 min. on the *E. coli* map and is designated tyrB. [Gelfand & Steinberg, J. Bact., 130, 429–440 (1977)]

As part of the present invention, it has been determined that the aspartate transaminase in certain *E. coli* (such as *E. coli* ATCC 11303) is enhanced and that conditions may be established which drive the reaction forward to allow yields of phenylalanine greater than 95% when used in the reaction:

EXAMPLE 7

In assays with *E. coli* mutants from the Yale collection the difference in the Keg for the different transaminases can be seen. Thus, while at 54 hours the ilvE mutant (CGSC #5502) showed 20% and the tyrB mutant (CGSC #5801) showed 33% conversion of phenylpyruvic acid to phenylalanine, the aspC mutant (CGSC #5798) showed 62% and *E. coli* ATCC 11303 showed 66% conversion in a free cell assay with glutamate as the amine donor. The ilvE mutant possesses only branched chain transaminases, while the tyrB mutant has a tyrosine repressible tyrosine/phenylalanine transaminase. The aspC mutant contains only the non-repressible aspartate transaminase.

When the free cell assay was carried out using 70% aspartic acid and 30% glutamic acid the conversion of phenylpyruvate to phenylalanine at 54 hours was 20% for the ilvE mutant, 57% for the tyrB mutant, 89% for *E. coli* ATCC 11303 and 91% for the aspC mutant.

The results for 70% aspartic acid/30% glutamic acid as the amine donor were nearly the same as those obtained when only L-aspartic acid was the amine donor. The ilvE mutant gave 19% conversion at 54 hours, the tyrB gave 57%, the aspC 100% and *E. coli* ATCC 11303 102%. It can thus be seen that aspartate transaminase is capable of giving much higher yields than expected on the basis of the literature and that these yields are significantly greater than those previously reported. Thus, as a further feature of the invention, it is proposed that phenylalanine be prepared from phenylpyruvic acid, or its equivalent, by contacting the same with aspartate transaminase. Advantageously *E. coli* ATCC 11303 is used for this purpose but other types of cells, free or immobilized, may also be employed.

EXAMPLE 8

In some cases, it may also be desirable to drive the reaction forward to the desired equilibrium condition of greater than 90% formation of phenylalanine. The use of *E. coli* ATCC 11303 with its inherently enhanced aspartate transaminase activity and the reaction condition prescribed is adequate to satisfy the indicated limitation as to the equilibrium conditions due to its lack of inhibition by the end products which is seen in the ilvE and tyrB mutants. On the other hand there may be situations where the aspartate transaminase does not by itself meet the desired equilibrium point. In that case, oxaloacetate decarboxylase may also be used to drive the equilibrium toward 100% conversions.

From an examination of the equilibrium equation for the reaction involved, determined by the equation:

$$K_{eq} = \frac{[PHE][OAA]}{[Asp][PPA]}$$

where OAA is oxaloacetate and PHE, Asp and PPA are as aforesaid, it can be seen that the reaction may be driven towards completion by removal of one of the products. Oxaloacetate decarboxylates under various conditions according to the reaction:

oxaloacetate→pyruvate+$CO_2$.

This reaction can effectively remove oxaloacetate from the equilibrium equation. When this reaction is coupled with the transamination, the equilibrium is driven toward completion.

HPLC determination of the level of oxaloacetate and pyruvate in the reaction was carried out on the product stream obtained from the varied conditions given in Table VI.

TABLE VI

| TIME (min) | OAA (MM) | PYR (MM) | PHE (MM) |
|---|---|---|---|
| 15 | 0.85 | 2.9 | 4 |
| 42 | 1.22 | 5.4 | 5 |
| 78 | 1.53 | 8.5 | 9 |
| 117 | 2.49 | 13.2 | 10 |
| 169 | 1.64 | 15.8 | 16 |
| 1350 | 3.20 | 55.4 | 77 |

The above data was taken from a batch reaction containing 25 ml of substrate (100 mM PPA, 150 mM ASP at pH 8.5) incubated with beads prepared as in Example 1 (containing 0.5 g cells, wet wt.) and rotary shaking at 37°.

When oxaloacetate was incubated under the following conditions, the decay rates were as shown:

| SOLVENT | PH | TEMP | OAA DECAY RATE (HALF-LIFE, min) |
|---|---|---|---|
| $H_2O$ | 2.3 | RT | 495 |
| $H_2O$ | 3.0 | RT | 113 |
| $H_2O$ | 10.1 | RT | 182 |
| $H_2O$ + 0.35 M $Na_2SO_4$ | 8.1 | 37° | 195 |
| $H_2O$ | 3.0 | 37° | 41 |
| Substrate | 7.6 | 37° | 14 |
| Substrate + catalyst | 7.7 | 37° | 14 |
| Substrate | 8.4 | 37° | 15 |

Thus, it will be appreciated that the conditions chosen for the reaction result in a rapid decomposition of oxaloacetate thus driving the reaction toward completion.

It will be appreciated that various modifications may be made in the invention described herein.

Accordingly, the scope of the invention is defined in the following claims wherein:

What is claimed is:

1. A process for preparing phenylalanine which comprises contacting a reaction mixture containing phenylpyruvic acid or phenylpyruvate, and aspartic acid or a combination of aspartic acid and glutamic acid, with aspartate transaminase present in *E. coli* ATCC 11303 and recovering phenylalanine in high yield from the reaction mixture.

* * * * *